United States Patent
Giles et al.

(10) Patent No.: US 10,388,499 B2
(45) Date of Patent: Aug. 20, 2019

(54) CONFIRMATION USING MULTIPLE COLLISION CROSS SECTION ("CCS") MEASUREMENTS

(71) Applicant: Micromass UK Limited, Wilmslow (GB)

(72) Inventors: Kevin Giles, Stockport (GB); Martin Raymond Green, Bowdon (GB); Keith Richardson, Derbyshire (GB); Jason Lee Wildgoose, Stockport (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 15/125,363

(22) PCT Filed: Mar. 10, 2015

(86) PCT No.: PCT/GB2015/050693
§ 371 (c)(1),
(2) Date: Apr. 3, 2017

(87) PCT Pub. No.: WO2015/136264
PCT Pub. Date: Sep. 17, 2015

(65) Prior Publication Data
US 2017/0131238 A1  May 11, 2017

(30) Foreign Application Priority Data

Mar. 10, 2014 (EP) .................................. 14158643
Mar. 10, 2014 (GB) .................................. 1404195.8

(51) Int. Cl.
*H01J 49/36* (2006.01)
*H01J 49/00* (2006.01)
*G01N 27/62* (2006.01)

(52) U.S. Cl.
CPC ........ *H01J 49/0036* (2013.01); *G01N 27/622* (2013.01); *H01J 49/004* (2013.01); *H01J 49/005* (2013.01); *H01J 49/0031* (2013.01)

(58) Field of Classification Search
CPC ............................ G01N 27/622; H01J 49/004
(Continued)

(56) References Cited

U.S. PATENT DOCUMENTS 6,495,824 B1   12/2002   Atkinson
6,831,273 B2   12/2004   Jenkins et al.
(Continued)

FOREIGN PATENT DOCUMENTS

WO   2004/012231   5/2004

OTHER PUBLICATIONS

Dwivedi et al., "Rapid Resolution of Carbohydrate Isomers by Electrospray Ionization Ambient Pressure Ion Mobility Spectrometry-Time-of-Flight Mass Spectrometry (ESI-APIMS-TOFMS)", Focus: From Mobilities to Proteomes, p. 1163-1175, Apr. 2007.

(Continued)

*Primary Examiner* — Michael Maskell (57) ABSTRACT

A method of identifying ions or confirming the identity of ions is disclosed comprising determining a physico-chemical or other property of first ions under first conditions, determining the physico-chemical or other property of the first ions or second ions derived from the first ions under second different conditions, and identifying or confirming the identity of the first ions or determining a class of the first or the second ions on the basis of the physico-chemical or other property of the first ions as determined under the first conditions and on the basis of the physico-chemical or other property of the first ions or second ions derived from the first ions as determined under the second conditions.

19 Claims, 2 Drawing Sheets

(58) Field of Classification Search
USPC .................. 250/281, 282, 286, 287, 290–293
See application file for complete search history.

(56) References Cited

U.S. PATENT DOCUMENTS

| | | | |
|---|---|---|---|
| 7,812,305 | B2 | 10/2010 | Miller et al. |
| 8,242,442 | B2 | 8/2012 | Krueger et al. |
| 8,278,620 | B2 | 10/2012 | Schwartz et al. |
| 8,384,024 | B2 | 2/2013 | Miller et al. |
| 8,525,106 | B2 | 9/2013 | Muntean |
| 8,618,475 | B2 | 12/2013 | Clemmer et al. |
| 8,921,778 | B2 | 12/2014 | Atkinson et al. |
| 2007/0114382 | A1 | 5/2007 | Clemmer et al. |
| 2010/0108877 | A1* | 5/2010 | Wu .................... G01N 27/622 250/282 |
| 2010/0127166 | A1* | 5/2010 | Krueger ............. G01N 27/622 250/282 |
| 2010/0224770 | A1 | 9/2010 | Burns et al. |
| 2013/0009053 | A1 | 1/2013 | Wu |
| 2013/0218478 | A1 | 8/2013 | Campuzano et al. |
| 2016/0054264 | A1 | 2/2016 | Carver et al. |

OTHER PUBLICATIONS

Green et al., "Modification of Ion Mobility Separation Using Volatile Organic Dopants on a Quadrupole-Ion Mobility-Orthogonal Time-Of-Flight Mass Spectrometer", Proceedings 59th ASMS, 2011.

Knapman et al., "Considerations in Experimental and Theoretical Collision Cross-Section Meansurements of Small Molecules Using Travelling Wave Ion Mobility Spectrometry-Mass Spectrometry", International Journal of Mass Spectrometry, Elsevier Science Publishers, vol. 298, No. 1-3, p. 17-23, Dec. 2010.

Lapthorn et al., "Ion Mobility Spectrometry-Mass Spectrometry (IMS-MS) of Small Molecules: Separating and Assigning Structures to Ions", Mass Spectrometry Reviews, vol. 32, No. 1, p. 43-71, Aug. 2012.

Shvartsburg et al., "An Exact Hard-Spheres Scattering Model for the Mobilities of Polyatomic Ions", Chemical Physics Letters, vol. 261, No. 1, pp. 86-91, Oct. 1996.

Williams et al., "Use of Ion Mobility Mass Spectrometry and a Collision Cross-Section Algorithm to Study an Organometallic Ruthenium Anticancer Complex and its Adducts with a DNA Oligonucleotide", RCM, p. 3563-3569, Jun. 2009.

Fernandez-Maestre R et al., "Buffer Gas Modifiers Effect Resolution in Ion Mobility Spectrometry Through Selective Ion-Molecule Clustering Reactions", Rapid Communications in Mass Spectrometry, vol. 26, No. 19, p. 2217-2222, Sep. 2012.

Fernandez-Maestre R et al., "Using a Buffer Gas Modifier to Change Separation Selectivity in Ion Mobility Spectrometry", Journal of Mass Spectrometry, vol. 298, No. 1-3, p. 2-9, Dec. 2010.

Bush M F et al., "Collision Cross Sections of Proteins and Their Complexes: a Calibration Framework and Database for Gas-Phase Structural Biology" Analytical Chemistry, vol. 82, No. 22, p. 9557-9565, Nov. 2010.

* cited by examiner

|    | Analyte          | [M+H]⁺    |
|----|------------------|-----------|
| 1  | 4-Acetamidophenol | 152.0712 |
| 2  | Caffeine         | 195.0882  |
| 3  | Sulfaguanidine   | 215.0603  |
| 4  | Carbofuran       | 222.1130  |
| 5  | Tolbutamide      | 271.1116  |
| 6  | Sulfadimethoxine | 311.0814  |
| 7  | Val-Tyr-Val      | 380.2185  |
| 8  | Verapamil        | 455.2910  |
| 9  | Terfenadine      | 472.3215  |
| 10 | Leucine Enkephalin | 556.2771 |
| 11 | Reserpine        | 609.2812  |

CONFIRMATION USING MULTIPLE COLLISION CROSS SECTION ("CCS") MEASUREMENTS

CROSS REFERENCE TO RELATED APPLICATIONS

This application is the National Stage of International Application No. PCT/GB2015/050693, filed 10 Mar. 2015 which claims priority from and the benefit of United Kingdom patent application No. 1404195.8 filed on 10 Mar. 2014 and European patent application No. 14158643.8 filed on 10 Mar. 2014. The entire contents of these applications are incorporated herein by reference.

FIELD OF THE INVENTION

The present invention relates generally to mass spectrometry and in particular to methods of identifying ions or confirming the identity of ions, methods of mass spectrometry, control systems for mass spectrometers and mass spectrometers.

BACKGROUND

The collision cross section ("CCS") of an ion measured using an ion mobility separator ("IMS") may be used to identify a target analyte when compared to a previously measured library value. Collision cross section may be used in conjunction with other measurements such as ionic mass and chromatographic retention time to add further specificity to compound identification.

It is desired to provide an improved method of identifying ions or confirming the identity of ions.

SUMMARY

According to an aspect there is provided a method of identifying ions or confirming the identity of ions comprising:

determining a physico-chemical or other property of first ions under first conditions;

determining the physico-chemical or other property of the first ions or second ions derived from the first ions under second different conditions; and identifying or confirming the identity of the first ions or determining a class of the first or the second ions on the basis of the physico-chemical or other property of the first ions as determined under the first conditions and on the basis of the physico-chemical or other property of the first ions or second ions derived from the first ions as determined under the second conditions.

It is not known to identify analyte ions on the basis of having determined the ion mobility of the analyte ions under two different conditions wherein e.g. the composition of a buffer gas is altered by, for example, adding an additive. Similarly, it is not known to identify analyte ions on the basis of having determined the ion mobility of the analyte ions under two different conditions wherein one or more operational parameters of an ion mobility spectrometer (e.g. transient DC voltage wave amplitude or effective velocity) may have been altered.

An embodiment allows more specificity in confirming the presence of target compounds by reducing false positive identifications.

An embodiment allows classes of compounds to be identified by, for example, observing a characteristic drift time shift of the ions when the ion mobility conditions are altered.

It is known to use a measurement of collision cross section in target confirmation. However, the accuracy of such measurements (±2%) can still result in a degree of ambiguity. Advantageously, the approach according to an embodiment significantly improves the accuracy of target confirmation.

The method according to an embodiment increases the accuracy of identifying analyte ions. In particular, according to an embodiment the drift time difference of analyte ions which are caused to separate temporally in the presence of buffer gases (which have different compositions) may be measured and the approach according to an embodiment is particularly advantageous in that it is substantially more robust to changes in the condition of the ion mobility separator than utilising an absolute drift time measurement. As a result, the disclosed approach results in a significant improvement in precision and accuracy.

It should be understood that the various disclosed embodiments are not limited to making just two measurements i.e. determining the physico-chemical or other property of first ions (or second ions derived from the first ions) under just two different conditions. Embodiments are contemplated wherein the physico-chemical or other property of the first ions (or second ions derived from the first ions) may be determined under third, fourth, fifth, sixth, seventh, eighth, ninth, tenth or further different conditions.

According to an aspect there is provided a method of mass spectrometry comprising:

providing analyte ions;

measuring or recording a value for specific analytes related to the analyte ions mobility in an electric field under a first set of conditions;

measuring or recording a value for specific analytes related to the analyte ions mobility in an electric field in the presence of a second substantially different set of conditions; and utilising more than one of the previously recorded values to confirm the identity of an analyte in a subsequent analysis or to indicate the class or chemical nature of an analyte.

The collision cross section value in each buffer gas composition may be recorded and the difference in collision cross section value between buffer gases may also be recorded. More than one measurement relating to ion mobility is may be made for a given analyte ion.

The drift time value in two more different buffer gas compositions may be recorded and the difference in drift time value between buffer gases may be recorded.

The physico-chemical or other property may comprise drift time, ion mobility drift time, ion mobility, differential ion mobility, collision cross section, interaction cross section, ion mobility peak shape, skew of an ion mobility peak or kurtosis of an ion mobility peak.

It will be understood that the skew and kurtosis of an ion mobility peak are not in themselves physico-chemical properties of the ions but nonetheless these shape metrics directly arise from or are otherwise due to the physico-chemical properties of the ions.

The step of determining a physico-chemical or other property of first ions under first conditions may comprise determining the physico-chemical or other property of the first ions in the presence of a first buffer gas.

The first buffer gas may comprise a first gas having a first composition.

The first gas may comprise one or more organic gases and/or one or more inorganic gases.

The first gas may comprise air, nitrogen, helium, carbon dioxide, oxygen, hydrogen, methane, argon, sulphur hexafluoride, acetylene, ammonia, benzene, butane, neon, nitrogen dioxide or sulphur dioxide.

The first gas may comprise one or more additives.

The one or more additives may comprise <1%, 1-2%, 2-3%, 3-4%, 4-5%, 5-6%, 6-7%, 7-8%, 9-10% or >10% by volume.

The one or more additives may comprise a volatile organic substance.

The step of determining a physico-chemical or other property of first ions or second ions derived from the first ions under second different conditions may comprise determining the physico-chemical or other property of the first ions or second ions derived from the first ions in the presence of a second different buffer gas.

The second buffer gas may comprise a second gas having a second composition, wherein the second composition is different to the first composition.

The second gas may comprise one or more organic gases and/or one or more inorganic gases.

The second gas may comprise air, nitrogen, helium, carbon dioxide, oxygen, hydrogen, methane, argon, sulphur hexafluoride, acetylene, ammonia, benzene, butane, neon, nitrogen dioxide or sulphur dioxide.

The second gas may comprise one or more additives.

The one or more additives may comprise <1%, 1-2%, 2-3%, 3-4%, 4-5%, 5-6%, 6-7%, 7-8%, 9-10% or >10% by volume.

The one or more additives may comprise a volatile organic substance.

The first ions may comprise parent or precursor ions.

The second ions may comprise fragment, product or adduct ions which are formed directly or indirectly from the first ions.

The method may further comprise determining an ion mobility drift time difference between the ion mobility drift time of the first ions under the first conditions and the ion mobility drift time of the first ions or second ions derived from the first ions under the second different conditions.

The method may further comprise determining an ion mobility drift time difference which is normalised to a measured drift time.

The method may further comprise determining an average measured ion mobility drift time which is compared to a predetermined ion mobility drift time.

The method may further comprise temporally separating the first ions and optionally second ions derived from the first ions according to their ion mobility or differential ion mobility in one or more ion mobility separators or spectrometers.

The one or more ion mobility separators or spectrometers may be arranged in series and/or in parallel.

The class of the first ions or the second ions may comprise lipids, peptides, enzymes, hormones, vitamins, amino acids, proteins, polypeptides, metabolites, carbohydrates, sugars, fatty acids, polysaccharides or steroids.

The class of the first ions or the second ions may comprise the charge state of the first ions and/or the charge state of the second ions.

According to an embodiment under the first conditions and/or under the second conditions ions may be subjected to activation, photo-activation, RF heating, irradiation, heating, microwave radiation, laser irradiation or electromagnetic radiation.

According to another aspect there is provided a method of mass spectrometry comprising a method as described above.

According to another aspect there is provided a control system of a mass spectrometer, wherein the control system is arranged and adapted:

(i) to determine a physico-chemical or other property of first ions under first conditions;

(ii) to determine the physico-chemical or other property of the first ions or second ions derived from the first ions under second different conditions; and (iii) to identify or confirm the identity of the first ions or determine a class of the first ions or the second ions on the basis of the physico-chemical or other property of the first ions as determined under the first conditions and on the basis of the physico-chemical or other property of the first ions or second ions derived from the first ions as determined under the second conditions.

According to another aspect there is provided a mass spectrometer comprising a control system as described above.

According to another aspect there is provided a method of identifying ions or confirming the identity of ions comprising:

determining a physico-chemical or other property of first ions;

determining the physico-chemical or other property of second ions derived from the first ions; and identifying or confirming the identity of the first ions or determining a class of the first ions or the second ions on the basis of the determined physico-chemical or other property of the first ions and on the basis of the determined physico-chemical or other property of the second ions derived from the first ions.

According to this aspect a physico-chemical property of first (e.g. parent or precursor) ions and second (e.g. first or further generation fragment) ions may be determined. The physico-chemical property may be the drift time or ion mobility drift time of the first (e.g. parent or precursor) ions and the drift time or ion mobility drift time of the second (e.g. first or further generation fragment) ions.

The physico-chemical or other property may comprise drift time, ion mobility drift time, ion mobility, differential ion mobility, collision cross section, interaction cross section, ion mobility peak shape, skew of an ion mobility peak or kurtosis of an ion mobility peak.

According to another aspect there is provided a method of mass spectrometry comprising a method as described above.

According to another aspect there is provided a control system of a mass spectrometer, wherein the control system is arranged and adapted:

(i) to determine a physico-chemical or other property of first ions;

(ii) to determine the physico-chemical or other property of second ions derived from the first ions; and (iii) to identify or confirm the identity of the first ions or determine a class of the first ions or the second ions on the basis of the determined physico-chemical or other property of the first ions and on the basis of the determined physico-chemical or other property of the first ions or second ions derived from the first ions.

The physico-chemical or other property may comprise drift time, ion mobility drift time, ion mobility, differential ion mobility, collision cross section, interaction cross section, ion mobility peak shape, skew of an ion mobility peak or kurtosis of an ion mobility peak.

According to another aspect there is provided a mass spectrometer comprising a control system as described above.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") on source; (viii) an Electron Impact ("EI") ion source; (ix) a Chemical Ionisation ("CI") on source; (x) a Field Ionisation ("FI") on source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; and (xxvi) a Solvent Assisted Inlet Ionisation ("SAII") ion source; and/or (b) one or more continuous or pulsed ion sources; and/or (c) one or more ion guides; and/or (d) one or more ion mobility separation devices and/or one or more Field Asymmetric ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xxii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Right mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then optionally to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer may further comprises a device arranged and adapted to supply an AC or RF voltage to the electrodes. The AC or RF voltage may have an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage may have a frequency selected from the group consisting of: (1) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.) MHz; (xxiii) 9.0-9.5 MHz; (xxiv) 9.5-10.0 MHz; and (xxv) >10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar (viii) 100-1000 mbar; and (ix) >1000 mbar.

BRIEF DESCRIPTION OF THE DRAWINGS

Various embodiments will now be described, by way of example only, and with reference to the accompanying drawings in which.

DETAILED DESCRIPTION

An embodiment will now be described with reference to FIGS. 1A and 1B which show the overlaid reconstructed mass mobilograms for the [M+H]+ molecular ions of eleven compounds which are listed in the table shown in FIG. 2.

The ion mobility drift time of the molecular ion of each of the eleven compounds is shown. It is well known that either by theoretical calculation or by applying a predetermined calibration the collision cross section of each of the eleven compounds can be calculated or otherwise determined on the basis of the measured ion mobility drift time of the ions.

Figure 1:
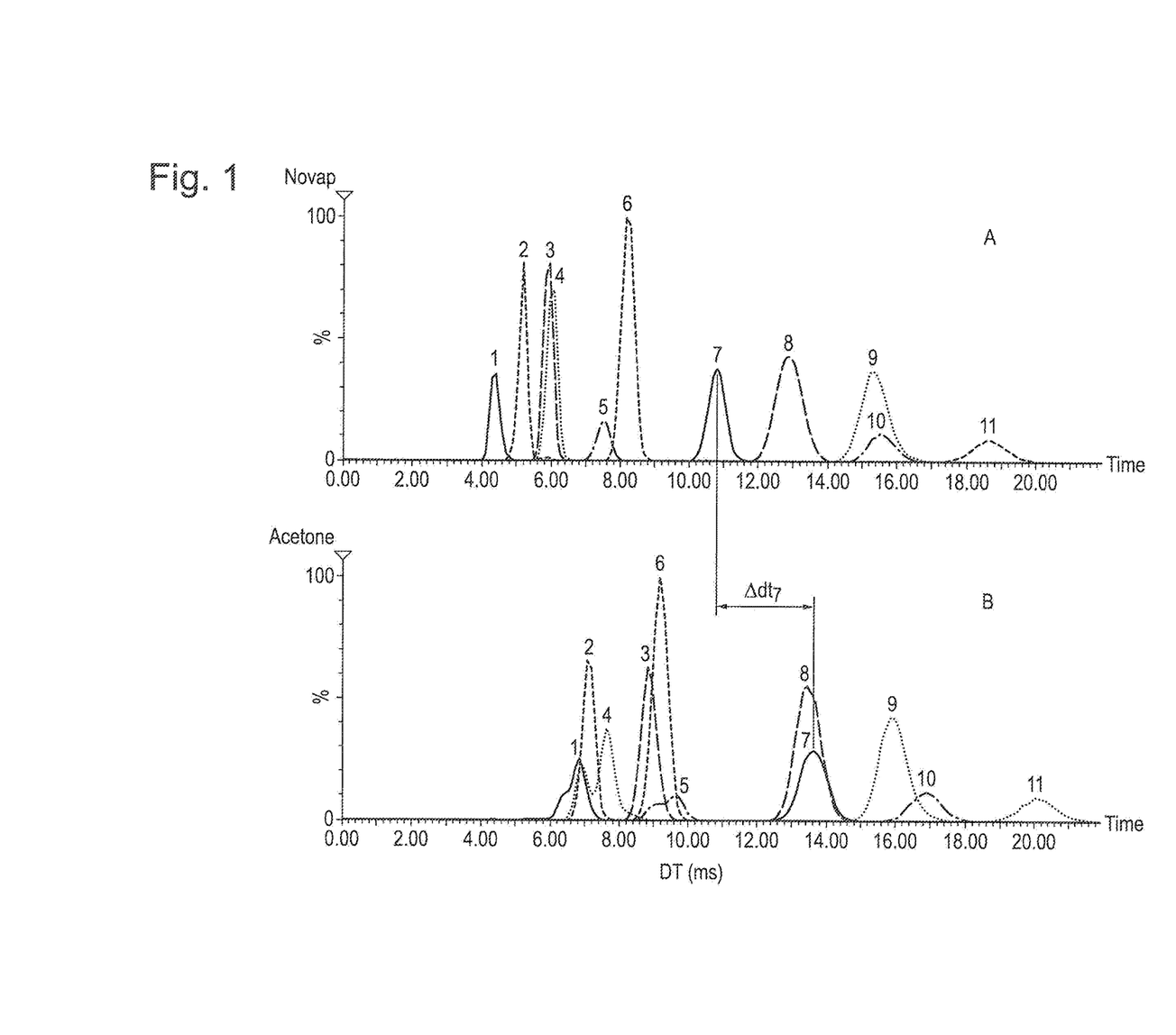
FIG. 1A shows overlaid reconstructed mass mobilograms for the [M+H]+ molecular ions of eleven compounds which are listed in the table shown in FIG. 2
FIG. 1B shows the overlaid reconstructed mass mobilograms for the [M+H]+ molecular ions of the eleven compounds when 1% acetone vapour was added to the buffer gas.

The overlaid reconstructed mass mobilograms for the eleven compounds shown in FIG. 1A were obtained by separating the ions according to their ion mobility using a travelling wave ion mobility separator wherein a pure nitrogen buffer gas was utilised. The buffer gas was maintained at a pressure of 2.5 mbar. The travelling wave ion mobility separator comprised a plurality of ring electrodes wherein ions were arranged to pass through the ring electrodes. Transient DC voltages or potentials were applied to the electrodes in order to urge ions axially along the length of the ion mobility separator or spectrometer. The amplitude of the transient DC voltages or potentials and the effective rate or speed at which the transient DC voltages or potentials were effectively translated along the length of the ion mobility spectrometer were arranged so that the analyte ions were separated according to their ion mobility.

FIG. 1B shows corresponding mobilograms for the same eleven compounds wherein the mobilograms were obtained under substantially similar conditions to the experiment described above with reference to FIG. 1A except that the buffer gas was altered through the addition of approximately 1% acetone vapour into the ion mobility separator cell so that the buffer gas comprised 99% nitrogen and 1% acetone vapour. The acetone was introduced via a septum inlet.

It is apparent from comparing the ion mobility drift times shown in FIG. 1B with the ion mobility drift times shown in FIG. 1A that all of the eleven analytes show a significant increase in ion mobility drift time due to the effects of the addition of 1% acetone vapour to the buffer gas. This general shift or overall general increase in the measured ion mobility drift time is due to the increase in the overall gas pressure which occurs when a volatile dopant vapour is introduced.

It is also clear from comparing FIG. 1B with FIG. 1A that different analytes have increased in ion mobility drift time (and hence also their apparent collision cross section) by different amounts. The shift or increase in drift time for each analyte will depend upon the nature of the electronic interaction between the analyte and the acetone molecules. The electronic interaction will also be different for different analytes. The relative shift in drift times will also be different if different buffer gas compositions are used. The shift in drift time therefore enables additional information relating to the analyte ions to be determined namely information relating to the nature of the electronic interaction between the analyte ions and the dopant.

Figure 2:
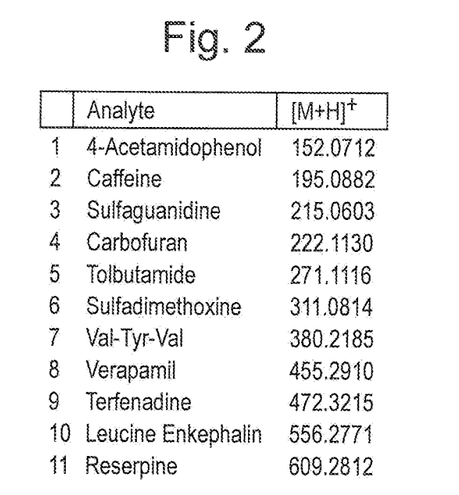
FIG. 2 lists the eleven compounds which were separately subjected to on mobility separation in the presence of different buffer gases and wherein the resulting mass mobilograms were reconstructed and are shown in FIGS. 1A and 1B.

The increase in ion mobility drift time $\Delta dt_7$ is indicated in FIG. 1B for the trip-peptide Val-Tyr-Val (which is indicated as peak 7 in FIGS. 1A and 1B and is listed as the seventh analyte in the table shown in FIG. 2).

The ion mobility drift time of an analyte in a buffer gas and the difference or shift in ion mobility drift time of the analyte due to a change of the composition of the buffer gas is very specific for each compound or analyte.

It is envisaged that for complex mixtures of analytes the ion mobility drift time of two different analytes may be substantially the same in a buffer gas having a particular composition. However, an advantage of an embodiment is that in such situations it is highly likely that the two (un-resolved) analytes will have different shifts in ion mobility drift time and/or different absolute values of ion mobility drift time when the analytes are subjected to ion mobility separation in a second (or subsequent) different buffer gas. The different shifts in ion mobility drift time will be due to different electronic interactions between the analytes and the dopant added to the buffer gas. The approach according to an embodiment therefore enables the presence of two or more analytes ions having substantially the same ion mobility drift times under a first set of conditions to be resolved when separating the ions under a second different set of conditions.

The above approach according to various embodiments greatly increases the specificity of drift time or collision cross section measurements for confirmation of target identity in a targeted analysis and significantly reduces the likelihood of false positives.

Multiple measurements of ion mobility under different conditions including the use of buffer gases having different compositions may be combined in various different ways in order to increase the confidence in confirmation of the presence of a target analyte or type or class of target analytes. According to an embodiment each absolute measurement may be compared to a calibrated prior measurement of a standard of the analyte under substantially the same experimental conditions. This method relies upon a valid calibration and/or a precise control of the conditions under which the calibration and subsequent targeted analysis are performed such that the drift time measured for the analytes under several different buffer gas compositions is substantially consistent within experimental error. Similarly, the differences in drift time or collision cross section which may be used to confirm the identity may be compared to an expected absolute difference.

Other methods of utilising the information are contemplated which are more robust to changes in absolute measured values. For example, the drift time difference may be normalised to the measured drift time to give a measure of the normalised drift time $DT_N$ wherein:

$$DT_N = \frac{2(DT_2 - DT_1)}{(DT_2 + DT_1)} \quad (1)$$

wherein $DT_1$ is the measured drift time of the analyte in a first buffer gas composition and $DT_2$ is the measured drift time of the analyte in a second buffer gas composition.

Alternatively, the average measured drift time may be calculated and compared to a prior measurement from a standard.

The methods described above relating to various embodiments may be extended to include further measurements in yet further different buffer gasses or under different experimental conditions.

According to an embodiment various operating conditions of the ion mobility separation such as the travelling wave height or travelling wave velocity of a travelling wave separator or the DC potential of a static DC ion mobility separator may be changed or varied resulting in the absolute values of drift time which are measured being different. The normalised drift time difference will still be specific for a given analyte as long as the buffer gas composition is controlled.

Other methods of normalisation are also envisaged. For example, if an internal or external known standard is introduced during calibration and subsequent analysis (e.g. lock mobility) such that the difference in drift time under different buffer gas conditions is measured and recorded during calibration for this reference compound, then a relative drift time $DT_R$ change value may be calculated:

$$DT_R = \frac{(DT_{S2} - DT_{S1})}{(DT_2 - DT_1)} \quad (2)$$

wherein $DT_1$ is the measured drift time of the analyte in a first buffer gas composition, $DT_2$ is the measured drift time of the analyte in a second buffer gas composition, $DT_{s1}$ is the measured drift time of the internal/external reference in the first buffer gas composition and $DT_{s2}$ is the measured drift time of the internal/external reference in the second buffer gas composition.

In this case, once initial calibration has been made, the value of $DT_R$ will be specific for a given analyte and will be sufficiently robust to slight variations in ion mobility separator conditions including buffer gas pressure and small changes in the composition of a mixed buffer gas such as the percentage of added acetone vapour. Additionally, this approach is more robust to ion mobility separation space charge saturation effects as shifts in drift time due to space charge effects will affect the differential or relative measurement of drift time less than the absolute measurements.

If more than two mobility measurements are made under more than two different conditions even more specificity may be achieved. In this case more than one mobility or drift time difference may be measured and may compared. The ratio of these may then be used to provide a characteristic value for a given species which is very robust to changes in experimental conditions.

The above methods may be used to differentiate between compound classes or charge states based on the general relative shift in drift time even if the absolute shift in drift time or even the identity of the analytes is unknown. For example, lipids and peptides will shift relative to each other in a characteristic way for a given buffer gas composition change. This relative shift may be used to identify these types of targets within a mixture.

It can be seen from FIGS. 1A and 1B that not only the ion mobility drift time of the analytes changes in a specific way but also the shape of the mobility peaks may also change in a specific way. Metrics associated with the peak shape under different buffer gas conditions may be calculated and may be used as an identification criteria or an additional identification criteria. For example, according to an embodiment skew and/or kurtosis and/or other complex curve fitting parameters and statistical or Bayesian analysis may be utilised in order to aid identification or to increase the confidence of a correct identification.

Various different methods of switching buffer gas composition may be utilised. For example, the composition of the buffer gas within a single ion mobility separator device may be changed by introducing a dopant or other gas via an inlet septum. The drift time and/or the collision cross section for analytes under each condition may be measured.

Alternatively, two or more separate parallel ion mobility separator devices may be provided wherein each ion mobility separator is provided with different buffer gas compositions. Ions are may sequentially switched into the two or more ion mobility separators or an ion beam may be split into two or more sub-beams wherein one sub-beam is directed to a first ion mobility separator and a second sub-beam is directed to a second ion mobility separator.

Figure 3:
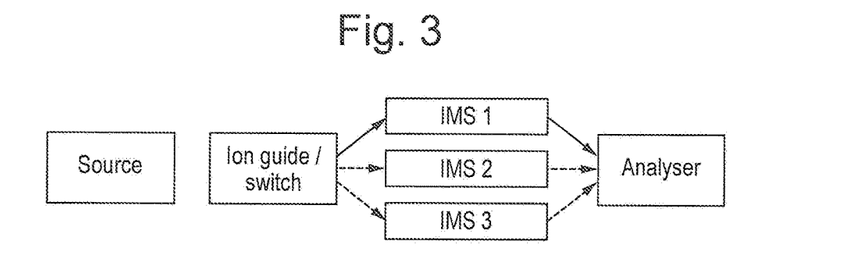
FIG. 3 shows an embodiment wherein a plurality of ion mobility separators are provided in parallel and wherein ions are either sequentially directed to different ion mobility separators or wherein an ion beam is split so that ions are simultaneously directed to each of the ion mobility separators.

FIG. 3 shows an embodiment wherein three ion mobility separators are provided in parallel. According to an embodiment ions may enter one of the ion mobility separator devices at a given time effectively bypassing the two other ion mobility separator devices. Alternatively, the ion beam may be split between the devices with a given portion of the ions being passed simultaneously to each ion motility separator device. The resultant ion mobility separator spectra may be analysed or recorded by different downstream devices (e.g. mass analysers) or by the same downstream device (e.g. mass analyser). In the latter case it may be necessary to introduce a known delay between either the start of an ion mobility separation cycle in each device or by introducing a delay in a device downstream of the ion mobility separators such that the signal from each device may be interrogated without interference.

Figure 4:
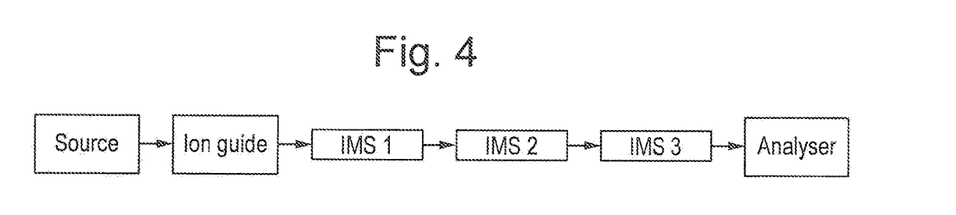
FIG. 4 shows another embodiment wherein a plurality of on mobility separators are provided in series and wherein ions are arranged to pass sequentially through the separate ion mobility separators.

FIG. 4 shows another embodiment wherein two or more ion mobility separator cells are arranged in series. The ion mobility separator cells may have different buffer gas compositions. Ions separated by the first ion mobility separator device with a first buffer gas may according to an embodiment be swept through the second or subsequent ion mobility separator device with no separation using relatively slow and/or relatively high amplitude travelling waves or transient DC voltage or potentials. Ions may then be passed through the first ion mobility separator device or devices as a continuous beam with no ion mobility separator separation and then separated in a subsequent ion mobility separator with a different buffer gas composition. Several measurements of collision cross section may be made.

According to an embodiment ions may be separated in an $n^{th}$ ion mobility separator device and then transferred into a subsequent $n+1^{th}$ ion mobility separator device whilst retaining the ion mobility separation from the $n^{th}$ ion mobility separator device.

This may be achieved using a transfer region between the two ion mobility separator devices at relatively low pressure and then utilising travelling waves or transient DC voltage or potentials or a DC ramp in order to maintain separation. Alternatively, a single device may be split such that a first part contains a first buffer gas composition and a second part contains a second different buffer gas composition. The pressure of buffer gas may be very similar in both regions. Ions may be urged through the device with or without ion mobility separation by appropriate selection of travelling wave parameters or parameters relating to the amplitude and/or frequency and/or velocity of one or more transient DC voltages or potentials.

According to the above embodiment the total drift time will be a combination of the drift time in the $n^{th}$ ion mobility separator device and the drift time in the $n+1^{th}$ ion mobility separator device. By using the ion mobility separator cells individually or in combination many different measurements of the same analyte may be made thereby increasing the confidence in a correct assignment.

Other embodiments are contemplated wherein two or more of the methods described above may be combined in series and/or in parallel.

An important aspect of an embodiment is that multiple ion mobility separator measurements may be taken under different conditions in order to increase the specificity of compound identification. Although changing buffer gas composition has been chosen to illustrate the general principle, the various embodiments are not restricted to varying the buffer gas composition.

Other methods of obtaining orthogonal ion mobility separation measurements to increase specificity include measuring the ion mobility of a parent or precursor ion and also measuring the ion mobility of corresponding product or fragment ions of a compound and using both ion mobility measurements to confirm the identity of the analyte. This technique can also be extended to $MS^n$ experiments wherein, for example, first, second, third or further generation fragment, daughter, product or adduct ions may be generated in a manner which is well known in the art. For example, according to an embodiment the ion mobility of a precursor or parent ion may first be measured. The precursor or parent ions can then be mass selected using an upstream quadrupole mass filter. The precursor or parent ions may then be fragmented or alternatively may be activated (e.g. photoactivated) and then an ion mobility measurement of the resulting product ions or fragment ions may be made using a downstream ion mobility separator device. The precursor and product ion mobilities may be used to confirm identity. The various embodiments may be extended to other geometries and also combined with the other methods described above.

It is possible to change the apparent collision cross section by introducing a source of energy into the ion mobility separator device as the ions are separated or by activating the ions prior to separation.

For example, a protein may be changed in conformation by activating the protein through collisions with a buffer gas. This change in collision cross section can also be used to confirm the presence of a target if the behaviour of the target ion under these conditions has been previously observed.

This change in collision cross section may be achieved by methods including RF heating, irradiation with laser light or other light source, heating the ion mobility separator directly or by microwave radiation.

The approach of using more than one measurement to identify target ions may be extended to ion mobility separator filtering devices such as Field Asymmetric Ion Mobility Spectrometry ("FANS") Differential Mobility Spectrometers ("DMS") and also Differential Mobility Analysers ("DMA"). In these devices there is a characteristic set of conditions under which ions will be transmitted through the device. For a given target these conditions may be measured in different buffer gas compositions and separate multiple measurements may be made to confirm the identity of the target ions.

It should be noted that the same general principle of using more than one measurement of drift time, collision cross section or other properties of the ions to differentiate between compound classes or charge state of the ions based on the general relative shift or difference in the measurements may also be applied to any one or more of the methods and examples described above.

Although the present invention has been described with reference to preferred embodiments, it will be understood by those skilled in the art that various changes in form and detail may be made without departing from the scope of the invention as set forth in the accompanying claims.

The invention claimed is:

1. A method of identifying a compound or analyte or confirming the identity of the compound or analyte comprising:
    determining a physico-chemical or other property of first ions under first conditions, said first ions being analyte ions of a specific compound or analyte;
    determining said physico-chemical or other property of said first ions under second different conditions, said first ions being analyte ions of said same specific compound or analyte;
    determining a difference value by determining a difference between the physico-chemical or other property of said first ions as determined under said first conditions and said physico-chemical or other property of said first ions as determined under said second conditions;
    recording the determined difference value; and
    identifying or confirming the identity of said specific compound or analyte or determining a class of said specific compound or analyte by comparing the recorded difference value to a previously measured library difference value, the previously measured library difference value comprising a difference between the physico-chemical or other property of ions as determined under said first conditions and said physico-chemical or other property of ions as determined under said second conditions.

2. A method as claimed in claim 1, wherein said physico-chemical or other property comprises drift time, ion mobility drift time, ion mobility, differential ion mobility, collision cross section, interaction cross section, ion mobility peak shape, skew of an ion mobility peak or kurtosis of an ion mobility peak.

3. A method as claimed in claim 1, further comprising ionizing said specific compound or analyte to produce the first ions, wherein:
the step of determining a physico-chemical or other property of first ions under first conditions comprises determining said physico-chemical or other property of at least some of said first ions in the presence of a first buffer gas; and
the step of determining a physico-chemical or other property of first ions under second different conditions comprises determining said physico-chemical or other property of at least some of said same first ions in the presence of a second different buffer gas.

4. A method as claimed in claim 3, wherein:
said first buffer gas comprises a first gas having a first composition; and
said second buffer gas comprises a second gas having a second composition, wherein said second composition is different to said first composition.

5. A method as claimed in claim 4, wherein:
said first gas comprises one or more organic gases and/or one or more inorganic gases; and/or
said second gas comprises one or more organic gases and/or one or more inorganic gases.

6. A method as claimed in claim 4, wherein:
said first gas comprises air, nitrogen, helium, carbon dioxide, oxygen, hydrogen, methane, argon, sulphur hexafluoride, acetylene, ammonia, benzene, butane, neon, nitrogen dioxide or sulphur dioxide; and/or
said second gas comprises air, nitrogen, helium, carbon dioxide, oxygen, hydrogen, methane, argon, sulphur hexafluoride, acetylene, ammonia, benzene, butane, neon, nitrogen dioxide or sulphur dioxide.

7. A method as claimed in claim 4, wherein:
said first gas comprises one or more additives; and/or
said second gas comprises one or more additives.

8. A method as claimed in claim 7, wherein said one or more additives comprises a volatile organic substance.

9. A method as claimed in claim 1, wherein said first ions comprise parent or precursor ions.

10. A method as claimed in claim 1, further comprising:
determining an ion mobility drift time difference value by determining an ion mobility drift time difference between the ion mobility drift time of said first ions under said first conditions and the ion mobility drift time of said first ions under said second different conditions, said first ions being analyte ions of said same specific compound or analyte;
recording the ion mobility drift time difference value; and
identifying or confirming the identity of said specific compound or analyte or determining a class of said specific compound or analyte by comparing the recorded ion mobility drift time difference value to a previously measured library ion mobility drift time difference value.

11. A method as claimed in claim 10, wherein the ion mobility drift time difference value comprises an ion mobility drift time difference which is normalised to an averaged drift time, and wherein the method comprises:
determining the normalised ion mobility drift time difference;
recording the normalised ion mobility drift time difference; and
identifying or confirming the identity of said specific compound or analyte or determining a class of said specific compound or analyte by comparing the normalised ion mobility drift time difference to a previously measured library normalised ion mobility drift time difference.

12. A method as claimed in claim 10, further comprising determining an average measured ion mobility drift time which is compared to a predetermined ion mobility drift time.

13. A method as claimed in claim 1, wherein said class of said first ions comprises lipids, peptides, enzymes, hormones, vitamins, amino acids, proteins, polypeptides, metabolites, carbohydrates, sugars, fatty acids, polysaccharides or steroids.

14. A method as claimed in claim 1, wherein said class of said first ions comprises the charge state of said first ions.

15. A control system of a mass spectrometer, wherein said control system is arranged and adapted:
(i) to determine a physico-chemical or other property of first ions under first conditions, said first ions being analyte ions of a specific compound or analyte;
(ii) to determine said physico-chemical or other property of said first ions under second different conditions, said first ions being analyte ions of said same specific compound or analyte;
(iii) to determine a difference value by determining a difference between said physico-chemical or other property of said first ions as determined under said first conditions and said physico-chemical or other property of said first ions as determined under said second conditions;
(iv) to record the determined difference value; and
(v) to identify or confirm the identity of said specific compound or analyte or determine a class of said specific compound or analyte by comparing the recorded difference value to a previously measured library difference value, the previously measured library difference value comprising a difference between said physico-chemical or other property of ions as determined under said first conditions and said physico-chemical or other property of ions as determined under said second conditions.

16. A method of identifying a compound or analyte or confirming the identity of the compound or analyte comprising:
determining a physico-chemical or other property of first ions, said first ions being analyte ions of a specific compound or analyte;
determining said physico-chemical or other property of second ions derived from said first ions, said second ions being analyte ions derived from said same specific compound or analyte;
determining a difference value by determining a difference between the determined physico-chemical or other property of said first ions and the determined physico-chemical or other property of said second ions derived from said first ions;
recording the determined difference value; and
identifying or confirming the identity of said specific compound or analyte or determining a class of said specific compound or analyte by comparing the recorded difference value to a previously measured library difference value.

17. A method as claimed in claim 16, wherein said second ions comprise fragment, product or adduct ions which are formed directly or indirectly from said first ions.

18. A method as claimed in claim 11, wherein the ion mobility drift time difference which is normalised to the averaged drift time is determined by:
- determining the ion mobility drift time difference between the ion mobility drift time of said first ions under said first conditions and the ion mobility drift time of said first ions under said second different conditions; and
- determining the average ion mobility drift time of said first ions under said first conditions and said first ions under said second different conditions; and
- normalising the ion mobility drift time difference with the average ion mobility drift time to determine the ion mobility drift time difference which is normalised to the averaged drift time.

19. A method as claimed in claim 1, further comprising ionizing said specific compound or analyte to produce the first ions, wherein:
- the step of determining a physico-chemical or other property of first ions under first conditions comprises determining said physico-chemical or other property of at least some of said first ions using a first transient DC voltage wave amplitude and/or a first transient DC voltage wave effective velocity; and
- the step of determining a physico-chemical or other property of first ions under second different conditions comprises determining said physico-chemical or other property of at least some of said same first ions using a second different transient DC voltage wave amplitude and/or a second different transient DC voltage wave effective velocity.

* * * * *